United States Patent [19]

Venooker et al.

[11] Patent Number: 5,586,590

[45] Date of Patent: Dec. 24, 1996

[54] COUPLER FOR FLUID DELIVERY SYSTEM

[75] Inventors: Ronald J. Venooker, Franklin; John A. Scavitto, Mendon; Peter N. Karkantis, Acton; David T. Healey, No. Reading; Richard L. Travers, Scituate, all of Mass.

[73] Assignee: Ciba Corning Diagnostics Corp., Medfield, Mass.

[21] Appl. No.: 513,697

[22] Filed: Aug. 11, 1995

Related U.S. Application Data

[62] Division of Ser. No. 165,137, Dec. 9, 1993, abandoned.

[51] Int. Cl.$^6$ ................................. B65D 47/00
[52] U.S. Cl. ........................ 141/386; 141/383; 141/18
[58] Field of Search ..................... 141/18, 21, 285, 141/346, 351–355, 383, 386, 289, 291, 292; 215/309–311, 276, 346, 352, 355; 220/303, 304, 373; 222/400.7, 464.1, 416; 137/212; 251/149.1, 149.3

[56] References Cited

U.S. PATENT DOCUMENTS

| | | |
|---|---|---|
| 1,482,373 | 1/1924 | Latremore . |
| 1,679,735 | 8/1928 | Murphy ................. 141/284 |
| 1,952,437 | 3/1934 | Huber . |
| 2,149,681 | 3/1939 | Johnston . |
| 2,190,054 | 2/1940 | Cutter et al. . |
| 2,288,565 | 6/1942 | Green ..................... 141/386 X |
| 2,526,630 | 10/1950 | Bourke . |
| 2,598,403 | 5/1952 | Macey . |
| 2,851,201 | 9/1958 | Poitras et al. ............ 222/481 |
| 2,992,762 | 7/1961 | Forman ................... 222/484 |
| 3,065,885 | 11/1962 | Chatten .................. 222/400.7 |
| 3,067,898 | 12/1962 | Reimann . |
| 3,084,823 | 4/1963 | Reichstein . |
| 3,157,323 | 11/1964 | Kitterman . |
| 3,438,553 | 4/1969 | Johnston ................. 222/400.7 |
| 3,460,569 | 8/1969 | Reinker . |
| 3,467,270 | 9/1969 | Eady . |
| 3,499,568 | 3/1970 | Riera . |
| 3,512,806 | 5/1970 | Romney et al. . |
| 3,596,810 | 8/1971 | Taubenheim ............. 222/400.7 |
| 3,904,059 | 9/1975 | Bellamy, Jr. et al. ..... 215/247 |
| 3,923,183 | 12/1975 | Choksi et al. ............ 215/251 |
| 4,022,205 | 5/1977 | Tenczar . |
| 4,065,018 | 12/1977 | Megowen et al. ......... 215/231 |
| 4,089,444 | 5/1978 | Shea ...................... 222/400.7 |
| 4,265,280 | 5/1981 | Ammann et al. .......... 141/98 |
| 4,265,363 | 5/1981 | Conn ...................... 215/229 |
| 4,320,911 | 3/1982 | Wood ..................... 285/89 |
| 4,433,973 | 2/1984 | Kurtz et al. .............. 604/403 |
| 4,576,199 | 3/1986 | Svensson et al. ......... 137/614.04 |
| 4,611,643 | 9/1986 | Beebe et al. ............. 141/311 R |
| 4,676,287 | 6/1987 | Fitzwater ................ 141/285 |
| 4,682,704 | 7/1987 | Kessler et al. ........... 215/329 |
| 4,715,359 | 12/1987 | Ryo . |
| 4,740,206 | 4/1988 | Allander . |
| 4,854,486 | 8/1989 | Daley et al. ............. 222/484 |
| 4,911,203 | 3/1990 | Garms .................... 137/614.04 |
| 4,941,519 | 7/1990 | Sestak et al. ............ 141/18 X |

(List continued on next page.)

FOREIGN PATENT DOCUMENTS

| | | |
|---|---|---|
| 0298376 | 1/1989 | European Pat. Off. . |
| 0477477 | 4/1992 | European Pat. Off. . |
| 0548570 | 6/1993 | European Pat. Off. . |
| 2364827 | 4/1978 | France . |

OTHER PUBLICATIONS

Ciba Corning Diagnostics Corp., Mechanical Drawing C009476.

*Primary Examiner*—J. Casimer Jacyna
*Attorney, Agent, or Firm*—Judith A. Roesler; Arthur S. Morgenstern

[57] ABSTRACT

A fluid delivery system for aspirating liquid from a bottle and conveying the liquid to an analytical instrument while allowing ambient air or gas to enter the bottle to replace the aspirated liquid. The bottle opening is sealed by a valve. A tube extends from the valve to the liquid within the bottle. A coupling component is removably connected to the analytical instrument anti to the valve for operatively connecting the instrument to the tube.

6 Claims, 10 Drawing Sheets

U.S. PATENT DOCUMENTS

| | | | |
|---|---|---|---|
| 4,946,455 | 8/1990 | Rosen | 604/403 |
| 4,982,736 | 1/1991 | Schneider . | |
| 5,029,624 | 7/1991 | McCunn et al. | 141/346 |
| 5,031,785 | 7/1991 | Lemme | 215/228 |
| 5,038,840 | 8/1991 | Fair | 141/383 X |
| 5,042,698 | 8/1991 | Fessell | 141/355 X |
| 5,145,094 | 9/1992 | Perlmutter | 222/153 |
| 5,297,599 | 3/1994 | Bucheli | 141/329 |
| 5,299,608 | 4/1994 | Bosyj | 141/285 |
| 5,323,832 | 6/1994 | Burrows | 222/484 X |
| 5,425,404 | 6/1995 | Dyer | 141/351 |

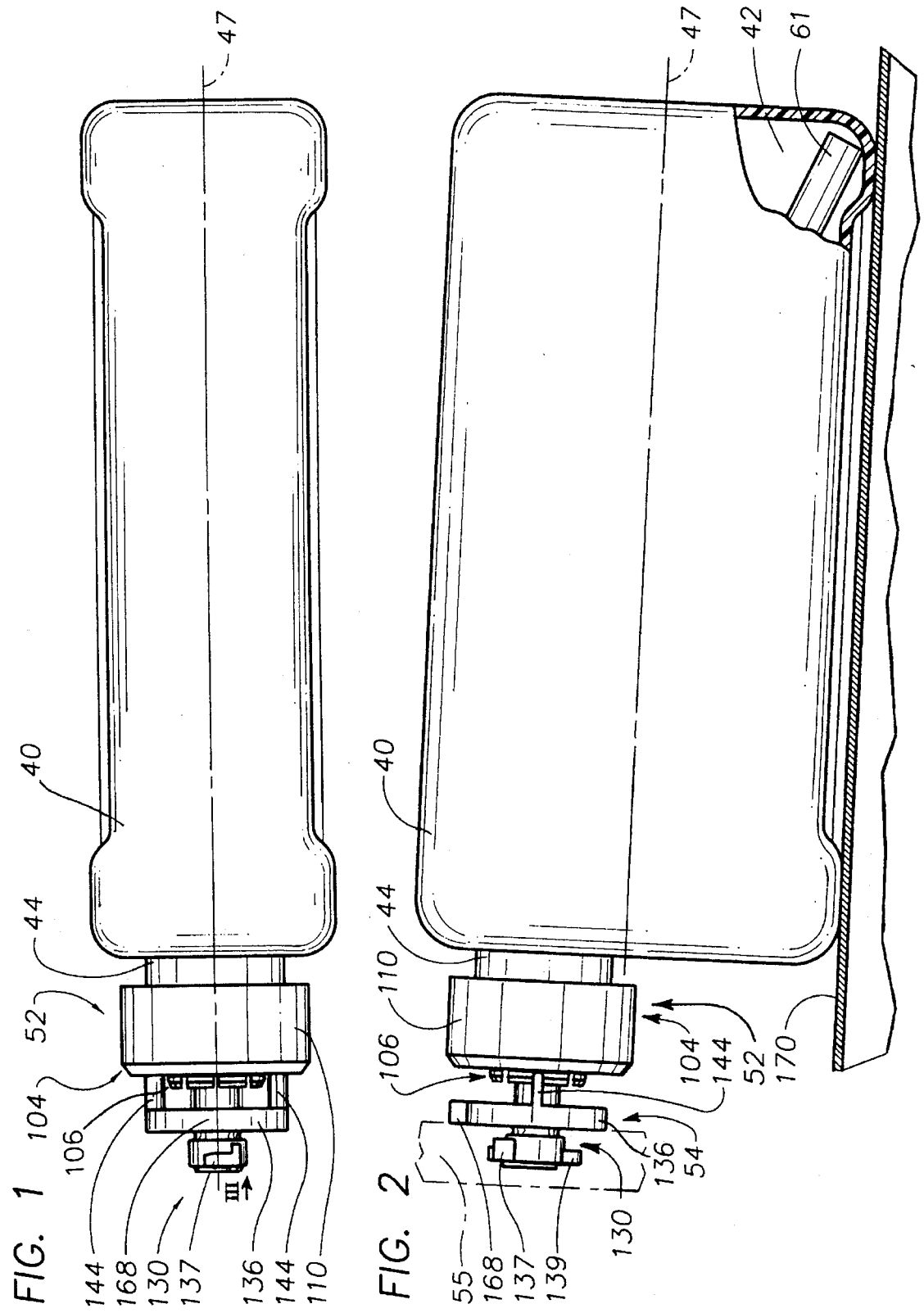

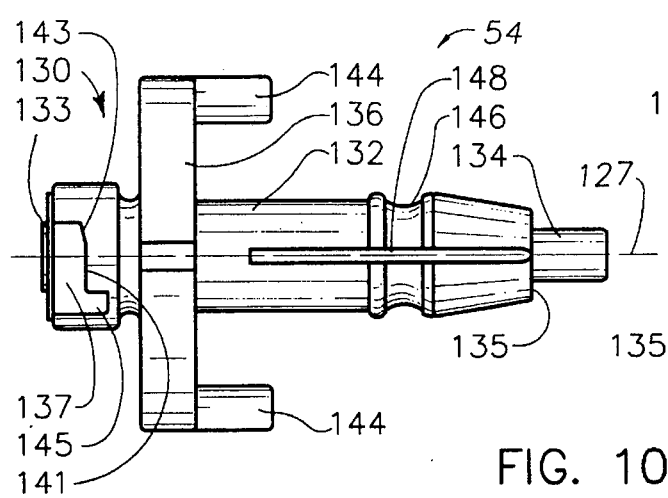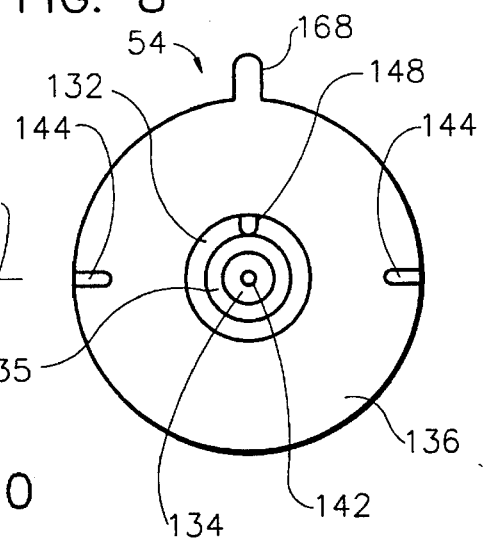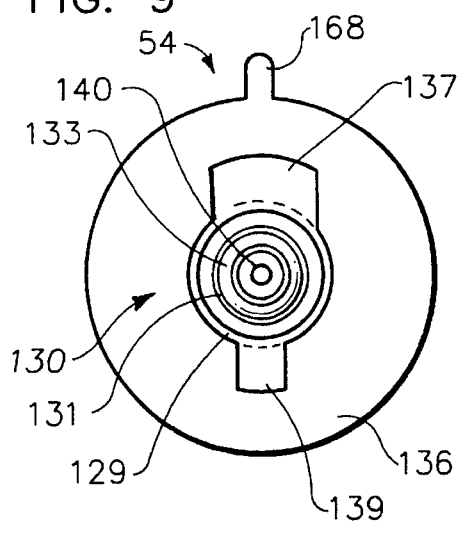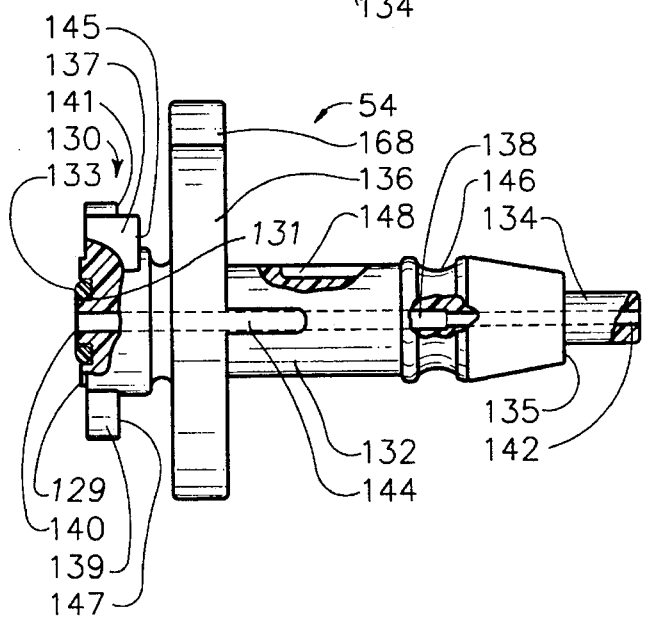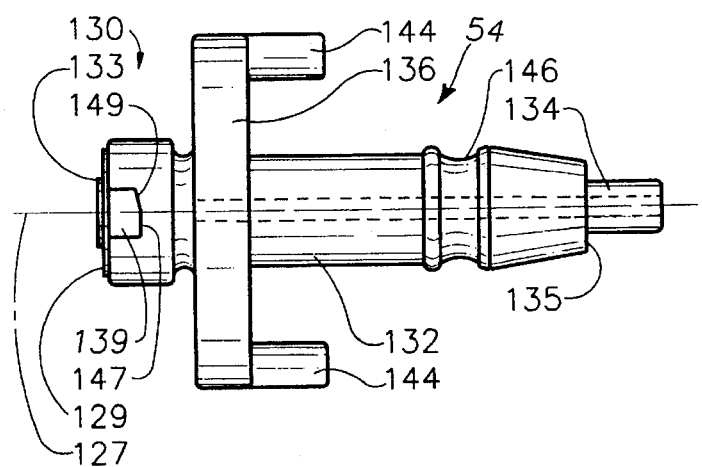

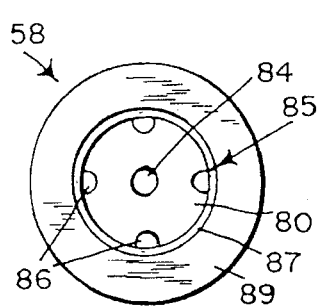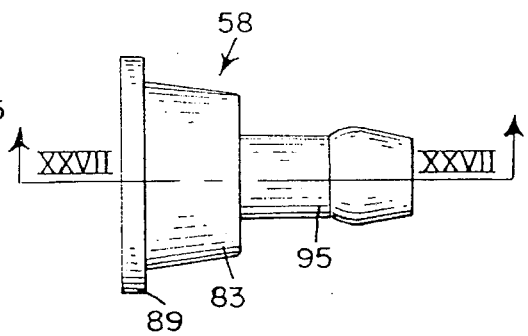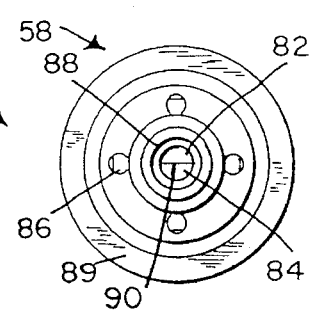
FIG. 24  FIG. 25  FIG. 26
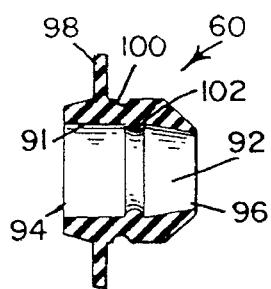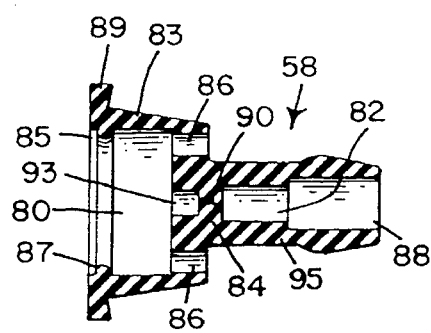
FIG. 31  FIG. 27
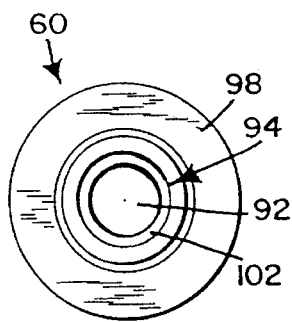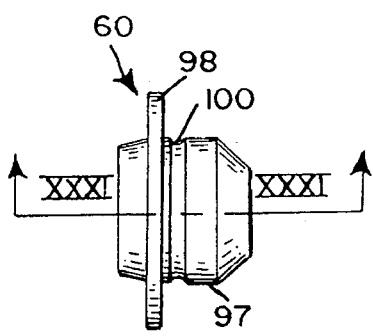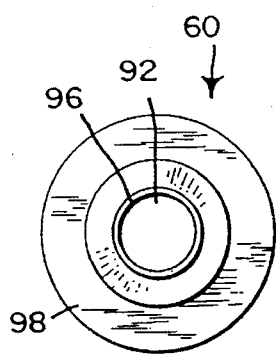
FIG. 28  FIG. 29  FIG. 30

COUPLER FOR FLUID DELIVERY SYSTEM

This is a divisional of application Ser. No. 08/165,137 filed on Dec. 9, 1993, and now abandoned.

TECHNICAL REVIEW

The present invention relates generally to a system for dispensing liquid from a container, such as a bottle. The invention is specifically directed to a system for aspirating liquid reagent from a container for use in analytical instruments. A preferred reagent bottle of the type described by the present invention includes an opening which is closed by a valve. A fluidic coupling component provides a fluidic connection between the valve and the analytical instrument. The analytical instrument includes a manifold to which the coupling is connected and means for creating suction at the manifold. The reagent is electively drawn from its container by the analytical instrument as needed in accordance with predetermined testing procedures. As reagent is drawn from the bottle air or gas must be introduced or vented into the bottle to replace the reagent. However the bottle must be sealed with respect to liquid and gas when reagent is not being drawn i.e. when the bottle is not attached to the instrument. A liquid seal must also be maintained during drawing of reagent from the bottle to prevent leakage of reagent to the outside of the bottle, i.e. when the bottle is attached to the instrument.

Known systems for delivery of liquids such as reagent which make use of needles or other fluid couplings or bayonet-like plungers have been less than satisfactory wit respect to sealing of the bottle during and between drawing of fluid from the bottle.

Creating an effective fluid seal at the point where the coupling component is connected to the analytical instrument is a necessary consideration.

Leaking around the cap of the bottle is another problem. Leaking is likely to occur if the cap is tightened too loosely following the filling of the bottle.

The process of replacing an empty reagent bottle with a full bottle remains a difficult and time-consuming step with some prior art systems. Care must be exercised to insure that all of the components of the system are properly connected to insure feeding of reagent from the bottle to the analytical instrument to insure proper sealing between interconnected components to prevent leaking of reagent from the system.

A liquid delivery system is shown in U.S. Pat. No. 4,854,486, issued 8 Aug. 1989 to Daley et al. The delivery system in the Daley patent includes a valve assembly for a container which has a bottom opening. A vent tube extends from the valve assembly to the top of the container. The delivery system also includes a probe which has a liquid passageway and a gas passageway. The probe is adapted to be inserted into the valve assembly so that the liquid from the container is able to flow from the container through the valve assembly and into the liquid passageway of the probe for eventual delivery to an analytical instrument. The gas passageway of the probe is operatively connected to the vent tube within the container so that air enters the container through the gas passageway and tube to replace the liquid which is withdrawn from the container. Although the liquid delivery system of Daley and the fluid delivery system of the present invention have some similar structural components, the two systems function in very different manners with respect to the flow of gas and liquid through the valve assembly and probe.

These and other difficulties experienced with the prior art devices have been obviated in a novel manner by the present invention.

Accordingly, it is principle object of the present invention to provide a fluid delivery system for an analytical instrument which maintains a gas and liquid seal to from the liquid container when the container is not attached to the analytical instrument and which maintains a liquid seal during drawing of liquid when the container is attached to the analytical instrument.

Another object of the invention is the provision of a fluid delivery system which has a first state wherein the system maintains a gas and liquid seal to and from the fluid container and a second or functional state which enables liquid to be drawn out of the container by the analytical instrument and air or other gas to be drawn into the container, from outside of the container.

A further object of the present invention is the provision of aspirating means for liquid such as reagent in which the opening to the container extends along a generally horizontal axis and insertion of the coupling means through said opening relative to the bottle is along a generally horizontal axis.

A still further object of the invention is the provision of a fluid delivery system in which a coupling component is removably connected at one end to the analytical instrument and the other end to the container and a fluid seal is created at both ends of the coupling component while allowing liquid to be aspirated from the container to the instrument and air to be drawn into the container from outside of the container to replace the aspirated liquid.

It is another object of the invention to provide a fluid delivery system in which the components of the system can be easily and accurately connected without loss of liquid, thereby enabling a depleted bottle to be easily replaced by a full bottle.

It is a further object of the invention to provide a cap assembly for a bottle which when used in conjunction with an elastomeric valve member or flange which prevents distortion of the valve member or flange as the valve member or flange is compressed by the cap assembly during tightening of the cap on the bottle.

Another object of the invention to provide a thrust washer for use with a cap for a bottle which is used in conjunction with an elastomeric valve member or flange, the thrust washer prevents distortion of the elastomeric valve member or flange as it is compressed by the thrust washer during tightening of the cap on me bottle.

It is a further object of the invention to provide a coupler for a fluid delivery system which is removably connected to a manifold fitting of an analytical instrument and to a fluid supply for selectively operatively connecting the fluid supply to the analytical instrument.

Another object of the invention is to provide a coupler which can be easily removed, without tools, for cleaning and disinfecting.

A further object of the invention to provide a valve housing for a fluid delivery system for aspirating liquid from a substantially horizontal bottle which has a substantially horizontal opening and conveying the liquid to an analyzing instrument and which cooperates with a valve at the bottle opening and tube for maintaining a liquid seal around one end of the tube and/or deflecting the tube downwardly at an angle from the valve to the bottom wall of the bottle.

It is a further object of the invention to provide a fluid delivery system for aspirating liquid from a bottle and for conveying the liquid to an analytical instrument in which the fluid delivery system enables the bottle to be substantially filed with liquid and which enables the liquid to be substantially completely aspirated from the bottle.

Another object of the invention to provide a coupler for a fluid delivery system which is connected to the manifold of an analytical instrument and to a reagent conduit for providing reagent to the manifold of the analytical instrument.

A further object of the invention is to provide a coupler to a manifold of an analytical instrument which on engagement to the manifold provides a fluid-tight connection.

With these and other objects in view, as will be apparent to those skilled in the art, the invention resides in the combination of parts set forth in the specification and covered by the claims appended hereto.

SUMMARY OF THE INVENTION

In general, the invention consists of a fluid delivery system for aspirating liquid from a container or bottle having an opening which is closed by a valve assembly having a first state, when the bottle is not attached to ion analytical instrument, for preventing the flow of gas and liquid into and out of the bottle and a second or functional state wherein gas is allowed to flow into the bottle from outside of the bottle and liquid is allowed to flow out of the bottle when the bottle is attached to an analytical instrument. The fluid delivery system also includes coupling means. The coupling means is operatively connected at one end to a manifold fitting of an analytical instrument. The coupling means includes a plunger at its opposite end for being selectively operatively connected at its other end to the valve assembly for rendering the valve assembly to the second state. The coupling means has a liquid passageway and a gas passageway. The liquid passageway enables liquid to be drawn or aspirated by the analytical instrument from the bottle through the valve assembly and the first passageway to the instrument. The gas passageway enables gas, such as ambient air to flow from outside of the bottle through the gas passageway and the valve assembly and into the interior space of the bottle to replace the volume of the aspirated liquid.

The invention also consists of a cap assembly for application to a threaded neck potion of a bottle which has a central longitudinal axis. The cap assembly includes a cap and a thrust washer. File cap has an end wall and a threaded side wall for screwing onto the threaded neck portion of a bottle. The thrust washer lies within the side wall against the end wall. The thrust washer is mounted on the cap so that the thrust washer is rotatable about the axis of the bottle neck relative to the cap.

The invention also includes a thrust washer for a cap which lies within the threaded side wall of the can and which is adapted to be mounted on the cap for rotation relative to the cap about the axis of rotation for the cap.

The present invention also consists of a coupler for operatively connecting a source of fluid or reagent to an analytical instrument. The coupler has a liquid passageway and a gas passageway. One end of the coupler enables the liquid passageway to be connected to a source of liquid to be aspirated. The other end of the coupler includes a connector fitting which is complementary with a manifold firing of the analytical instrument for operatively connecting the manifold fitting to the liquid passageway.

The invention also consists of a valve housing for a fluid delivery system in which liquid is aspirated from a container or bottle and conveyed to an analyzing instrument. The housing has a cylindrical primary bore for receiving a valve and a secondary bore which extends at a downward angle from the primary bore for receiving one end of a tube. The housing is adapted for insertion into a horizontally extending bore within the neck portion of a bottle which contains the fluid to be aspirated. The central longitudinal axis of the: bore is parallel to the generally horizontal central longitudinal axis of the bottle. The tube extends from the secondary bore at a downward angle from the valve housing to the lower most bottom wall of the bottle.

The invention also consists of a valve assembly for a fluid delivery system for aspirating liquid from a container or bottle and conveying the liquid to an analyzing instrument. The valve assembly includes a valve housing which is adapted for insertion into a generally horizontally extending bore of the neck of a bottle which contains the fluid to be aspirated. The valve housing contains a primary bore which extends along a generally horizontal central longitudinal axis and a secondary bore which extends from the primary bore at a downward angle relative to the central axis of the primary bore. The valve assembly also includes an elongated tube and an elastomeric valve which is located in the primary bore. The valve includes a flexible neck portion which extends into the secondary bore and which contains a socket for receiving one end of the tube. The tube extends at a downward angle relative to the central axis of the primary bore down to the bottom wall of the bottle. The flexible neck potion of the valve forms a liquid seal at the secondary bore between the housing and the tube.

A coupler for an aspirating fluid delivery system for conveying liquid from a source of liquid to be aspirated to a manifold fitting on an analytical instrument, said coupler comprising: a main body portion which has a central longitudinal axis, an elongated outer surface which is substantially parallel to said longitudinal axis, and an elongated liquid passageway which is substantially parallel to said longitudinal axis; a first end portion at one end of said main body portion which has a first end opening to said liquid passageway for operatively connecting said liquid passageway to said source of liquid; and a second end portion at the opposite end of said main body portion from said one end, said second end portion having a connector fitting which is complementary with said manifold fitting, said connector fitting having a second end opening to said liquid passageway for connecting said liquid passageway to said manifold fitting.

BRIEF DESCRIPTION OF THE DRAWINGS

The character of the invention, however, may be best understood by reference to one of its structural forms, as illustrated by the accompanying representative drawings,in which: FIG. 1 is a top plan view of a reagent bottle to which the fluid delivery system of the present invention is operatively connected, FIG. 2 is a side elevational view of the reagent bottle and fluid delivery system, FIG. 7 is a top plan view of the coupling means, FIG. 8 is an end view of the coupling means looking from the right of FIG. 7, FIG. 9 is an end view of the coupling means looking from the left of FIG. 7, FIG. 10 is a side elevational view of the coupling means, FIG. 11 is a bottom plan view of the coupling means, FIG. 24 is an outer end view of a first valve member and which forms part of the valve assembly, FIG. 25 is a top plan view of the first valve member, FIG. 26 is an inner end view of the first valve member, FIG. 27 is a vertical cross-sectional view of the first valve member, taken along the line XXVII—XXVII of FIG. 25 and looking in the direction of the arrows, FIG. 28 is an outer end view of a second valve member which forms part of the valve assembly, FIG. 29 is a top plan view of the second valve member, FIG. 30 is an inner end view of the second valve member, and FIG. 31 is a vertical cross-sectional view of the second valve member taken along the line XXXI—XXXI of FIG. 29 and looking in the direction of the arrows.

DETAILED DESCRIPTION OF THE INVENTION

Figure 3:
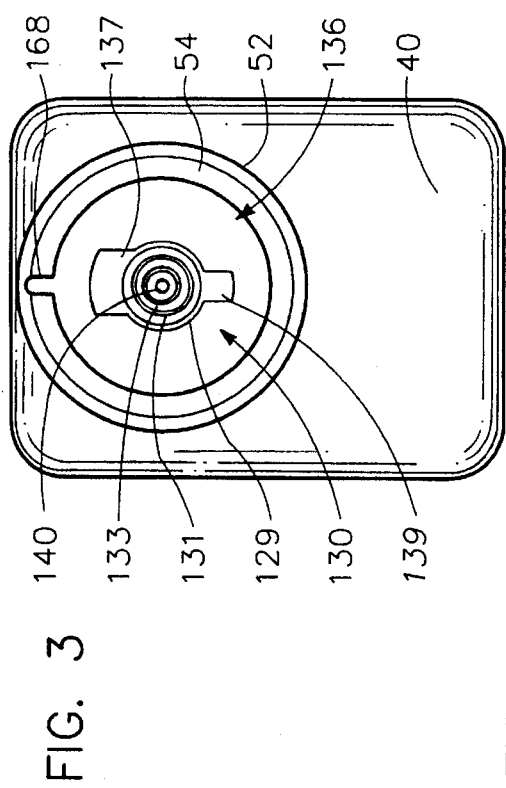
FIG. 3 is an end view of the reagent bottle and the fluid delivery system, looking in the direction of arrow III of FIG. 1.
Figure 4:
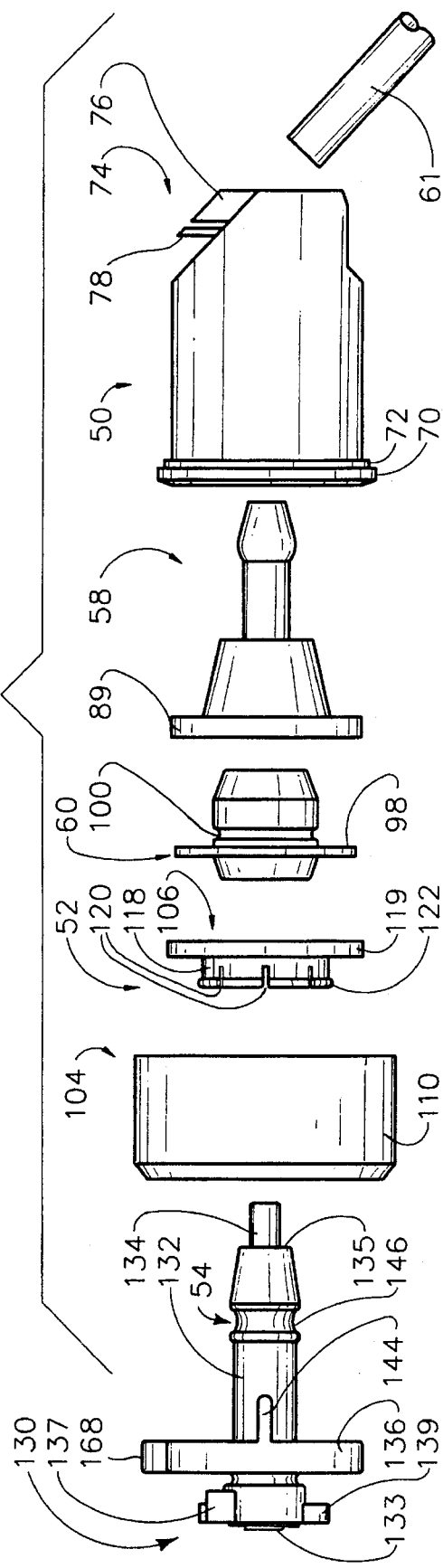
FIG. 4 is an exploded side elevational view of the coupling means and all of the individual elements of the valve assembly.
Figure 5:
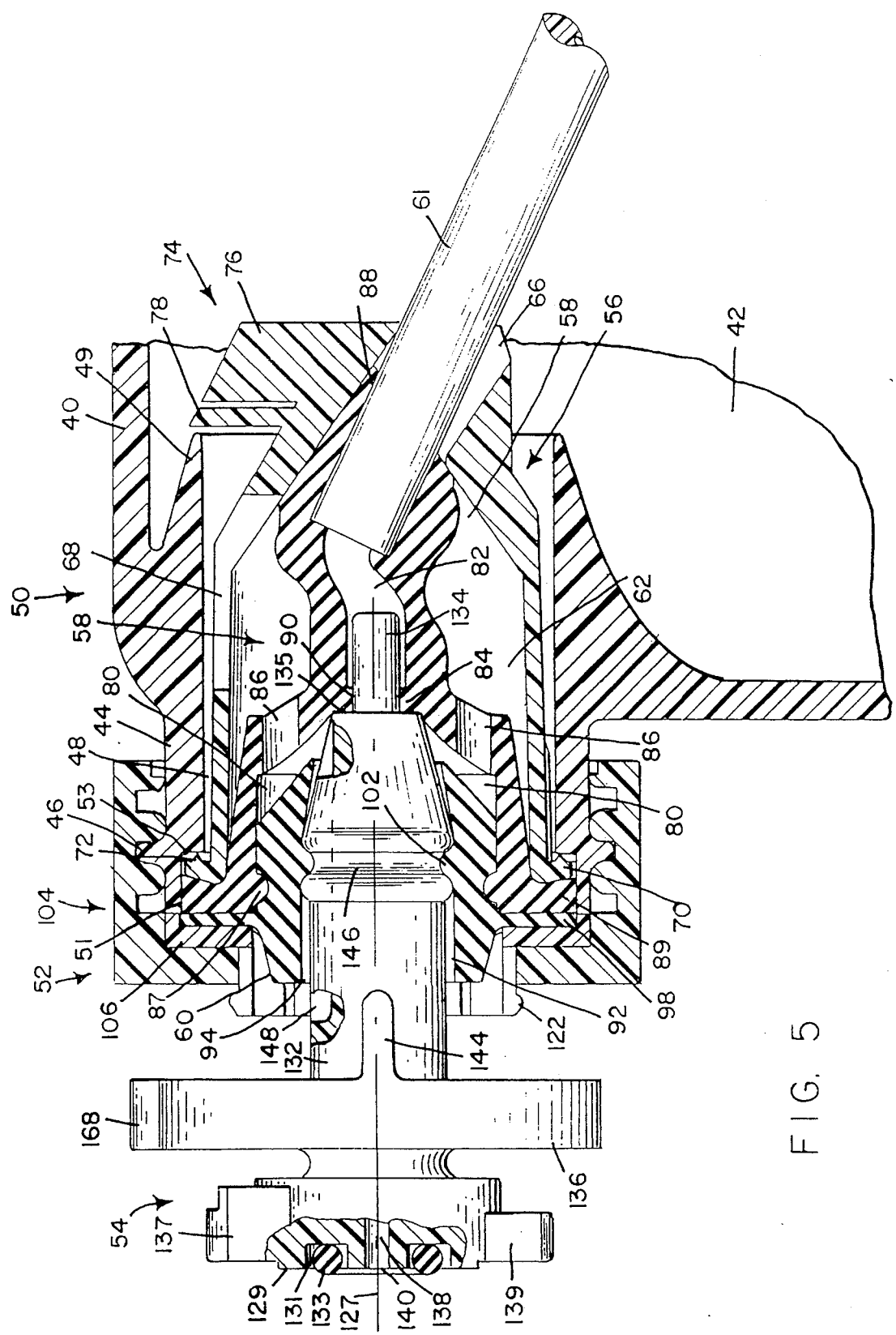
FIG. 5 is vertical cross-sectional view of the coupling means and valve assembly.

Referring first to FIGS. 1–5, the valve assembly of the present invention is generally indicated by the reference numeral 50. The coupling means is generally indicated by the reference numeral 54. The cap assembly is generally indicated by the reference numeral 52. The valve assembly 50, the coupling means 54 and the cap assembly 52 are operatively connected to a reagent bottle 40 which has an interior space 42, a bottom wall 45, and a neck portion 44. As shown in FIG. 5, the neck 44 of the bottle 40 has a horizontal bore 48 which extends from the outer open end of the neck to the interior space 42. The neck 44 has external threads 46 which are spaced from the opening 4.8. A tubular inwardly-extending projection or "blowdown" 49 extends from the neck portion 44 into the space 42 and represents one part of locking means for the valve assembly which is described hereinafter. The "blowdown" 49 is formed as a result of the plastic molding process anti is shown somewhat exaggerated in FIG. 5. The bottle 40 has a central longitudinal axis 47 and is designed to be supported in a generally horizontal position but at a slight angle to the horizontal as shown in FIG. 2. Also, the neck portion 44 is substantially above the central longitudinal axis 47 of the bottle.

Referring particularly to FIG. 4, the cap assembly 52 comprises a cap which is generally indicated by the reference numeral 104 and a thrust washer which is generally indicated by the reference numeral 106. The valve assembly 50 comprises a housing, a first embodiment of which is generally indicated by the reference numeral 56, a first valve member which is generally indicated by the reference numeral 58, a second valve member which is generally indicated by the reference numeral 60 and a tube 61 which extends from the valve assembly 50 into the interior assembled operative positions in FIG. 6 and are shown operatively connected to the coupling means 54 in FIG. 5.

Referring specifically to FIGS. 12–16, the housing 56 has a cylindrical main body portion, generally indicated by the reference numeral 69, which contains a primary bore 62 which has an air vent 68. The housing 56 has an outer end portion, generally indicated by the reference numeral 67, which contains an outer opening 64 to the primary bore 62 and an inner end portion, generally indicated by the reference numeral 71, which contains a secondary bore 66. In the preferred embodiment, the main body portion 69 tapers slightly from a relatively large diameter at the outer end portion 67 to a relatively small diameter at the inner end portion 71. The primary bore 62 has a horizontal central longitudinal axis 59. The secondary bore 66 extends at a downward angle from the primary bore 62 to an inner opening 73. The bore 62 constitutes a first chamber. The outer opening 64 constitutes a first outer opening of the first chamber. The secondary bore 66 and opening 73 constitute a first inner opening of the first chamber. The air vent 68 is located at the top of the bore 62 and constitutes a first intermediate opening 64 the bore or first chamber. A cam surface 65 extends at a downward angle from the primary bore 62 to the secondary bore 66. An annular bead 72 is located on the inwardly facing surface of the flange 70. Tab means, generally indicated by the reference numeral 74, is located at the inner end of the housing 56. Tab means 74 comprises a relatively stiff inner tab 76 and a deflectable resilient outer tab 78 which is slightly spaced from the tab 76. Tabs 76 and 78 extend transversely of the axis 59. The housing 56 is preferably made of a substantially rigid thermoplastic material. In the preferred embodiment, the housing is formed by injection molding. The material is sufficiently rigid so that the tab 76 which is relatively broad along a line which is parallel with the longitudinal axis 59 of the housing 56 is substantially non-deflectable. In contrast; the portion 78 which is relatively narrow along a line which is parallel with the central longitudinal axis 59 of the housing is substantially resiliently deflectable. The deflectable outer tab 78 extends further from the central longitudinal axis 59 of the housing than the relatively stiff inner portion 76. When the housing is inserted through the opening of the bottle 40, the tab 76 passes freely within the confines of the tubular, projection 49, while the resilient tab 78 is deflected by the interior surface of the projection 49 away from the inner tab and toward the axis 59. When the housing reaches the end of the tubular projection 49, as shown in FIG. 5, the tab 78 returns to its normal position adjacent the tab 76. Movement of the housing toward the opening 48 of the bottle causes the tab portion 78 to engage the projection 49 and to deflect the tab 78 toward the tab 76. However, since the tabs 78 and 76 are slightly spaced with respect to each other, the tab 78 will be deflected a slight amount until it engages the adjacent edge surface of the tab 76. At this point, further deflection of the tab 78 is prevented and no further outward movement of the housing 56 is possible. Therefore, the tab means 74 and a tubular projection 49 constitute cooperating locking means for the value assembly 52 which enables the valve assembly to be inserted into the bottle 40 and which prevents the housing from being withdrawn from the bottle after it has been fully inserted. A housing to bottle joint (press or press and weld) is established to prevent torque transmitted from the cap tightening operation from rotating the housing such that downward deflection of the tube is not altered.

Figure 35:
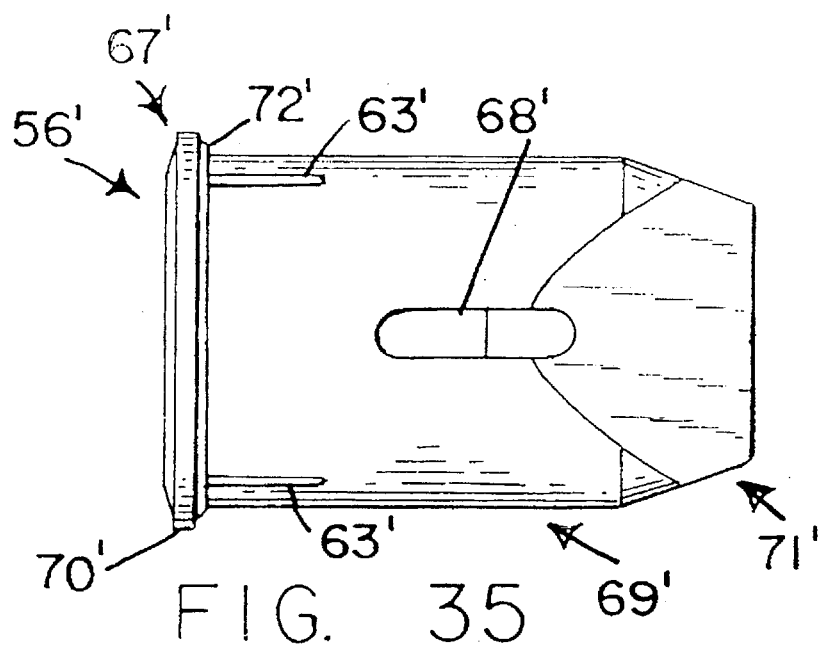
FIG. 35 is a top plan view of the modified valve assembly housing.
Figure 36:
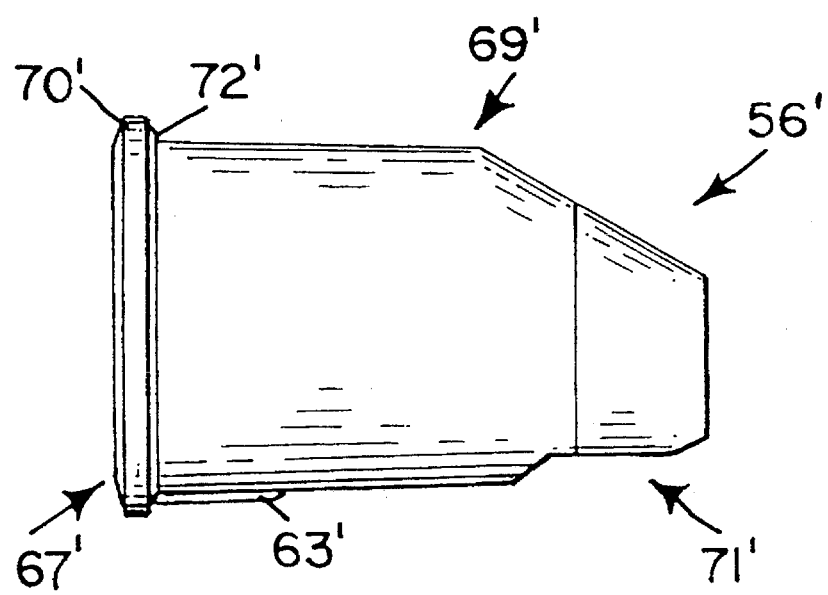
FIG. 36 is a side elevational view of a modified valve assembly housing.

A second embodiment of the valve housing is illustrated in FIGS. 35 and 36 and is generally indicated by the reference numeral 56'. Housing 56' is identical to housing 56 except that housing 56' does not have tab means 74. The housing is pressed into the bottle neck. All features of housing 56' which are identical with features of housing 56 are identified with the same reference numeral with the addition of a prime after the numeral.

Referring specifically to FIGS. 24–27, the first valve member 58 is made of an elastomeric material and comprises a relatively large diameter head portion 83 and a relatively small diameter flexible neck portion 95. The head portion 83 contains an outer second chamber 80 which has a second outer opening 85 and an annular ridge 87 which is adjacent the opening 85. An annular external flange 89 is located adjacent the second outer opening 85. The neck portion 95 has an inner second chamber 82 which has a second inner opening or socket 88. The outer and inner second chambers 80 and 82, respectively, are separated by a penetrable wall 84. A slit 90 is located in the wall 84 and extends from the chamber 82 to a relatively small diameter bore 93 which is connected to the chamber 80. The slit 90 is normally closed when the valve is in a first state due to the resilient nature of the valve member 58, so that the wall 84 normally provides a seal between the chambers 80 and 82. However, the slit 90 can be physically forced through an interference tit to an open position to create an opening between the outer and inner chambers 80 and 82, respectively, when the value is in a second or functional state. The chamber 80 is also connected to the outside of the valve member 58 by a plurality of air ducts 86 in the wall 84.

Referring to FIGS. 28–31, the second valve member 60 comprises an elastomeric body which has an outer surface 97 and a third chamber 92. The chamber 92 has a third outer opening 94 and a third inner opening 96. An annular groove 100 is located in the outer surface 97. An annular ridge 102 extends from the inner surface 91 which defines the third chamber 92. The ridge 102 extends into the chamber 92 at a point approximately mid-way between the outer and inner openings 94 and 96, respectively. An annular flange 98 extends around the outer periphery of the valve member 60 between the outer opening 94 and the annular groove 100.

Figure 6:
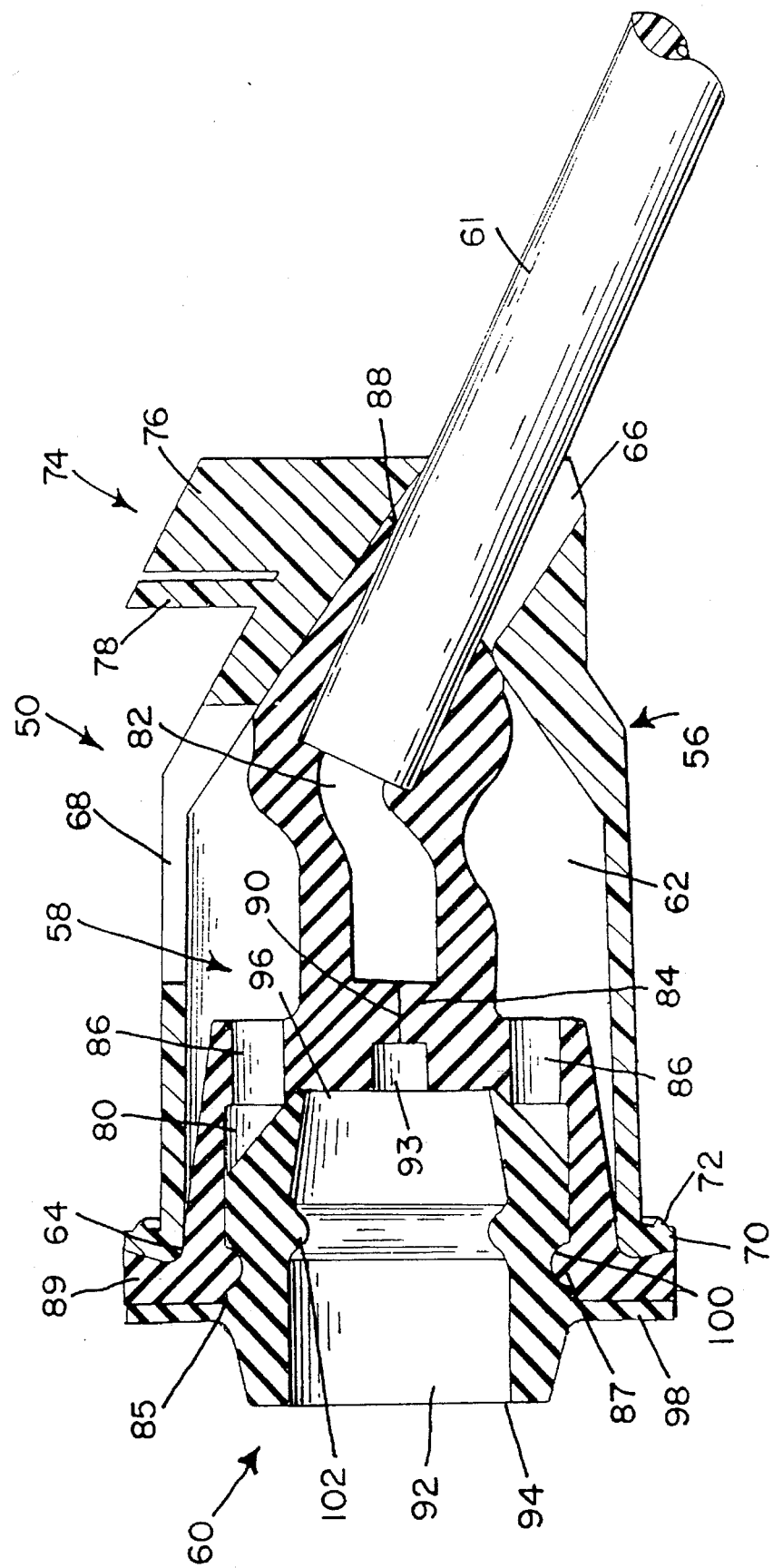
FIG. 6 is a vertical cross-sectional view of the valve assembly.
Figure 12:
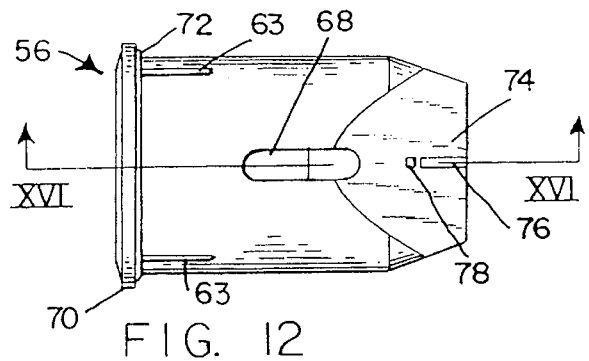
FIG. 12 is a top plan view of the housing portion of the valve assembly.
Figure 13:
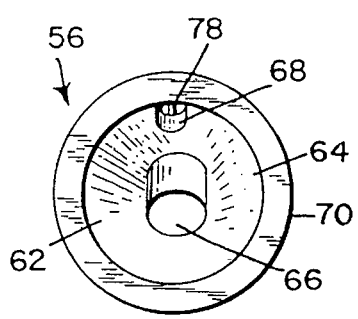
FIG. 13 is an end view of the housing, looking from the left of FIG. 12.
Figure 14:
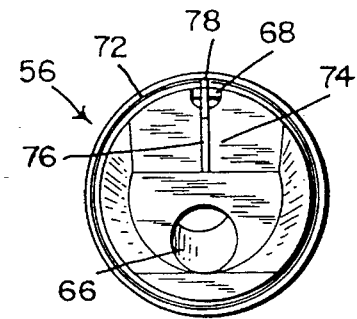
FIG. 14 is an end view of the housing looking from the fight of FIG. 12.
Figure 15:
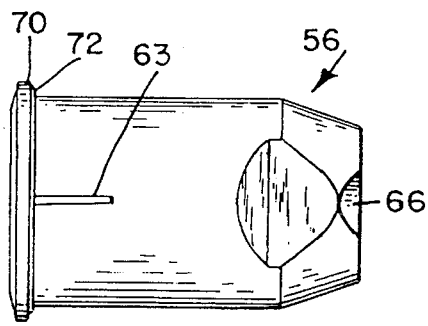
FIG. 15 is a bottom plan view of the housing.
Figure 16:
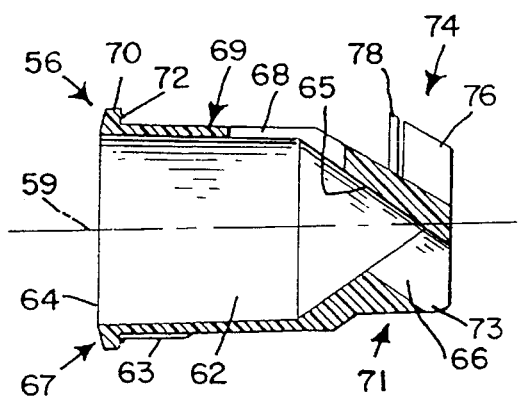
FIG. 16 is a vertical cross-sectional view of the housing, taken along the line XVI—XVI of FIG. 12.
Figure 17:
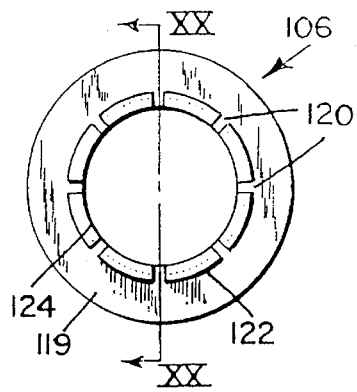
FIG. 17 is an outer end view of a thrust washer which is part of the cap assembly that holds the valve assembly to the bottle.
Figure 18:
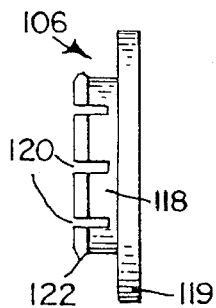
FIG. 18 is a side elevational view of the thrust washer.
Figure 19:
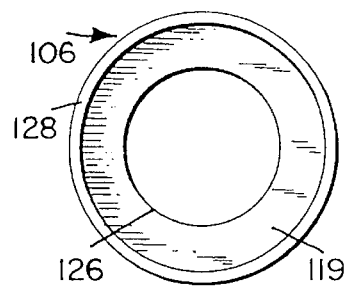
FIG. 19 is an inner end view of the thrust washer.
Figure 20:
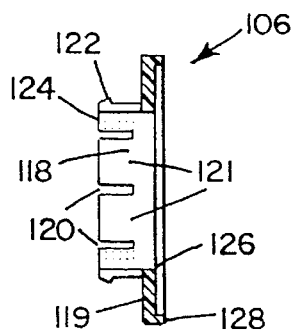
FIG. 20 is a vertical cross-sectional view of the thrust washer taken along the line XX—XX of FIG. 17 and looking in the direction of the arrows.

The second valve member 60 is designed to be inserted within the outer second chamber 80 of the first valve member 58, wherein the first annular ridge 87 of the valve member 58 engages the groove 100 of the valve member 60. This ensures that the valve members 60 is properly located or seated within the chamber 80 in a predetermined position. In this predetermined position, the third inner opening 96 is closed by the wall 84. The opening 96 is horizontally aligned with the inner second chamber 82 and can be operatively connected to the chamber 82 through the hole 93 and the slit 90. However, since the slit 90 is normally closed, the chamber 80 is normally sealed from the chamber 82. When the valve member 60 is inserted within the valve member 58, the flanges 98 and 89 abut as shown in FIG. 6. One end of the tube or straw 61 is inserted into the socket 88. The joined valve members 60 and 58 are then inserted into the first chamber or primary bore 62 of the housing 56 so that the flange 89 is located between the flanges 70 and 98 as shown in FIG. 6. The free end of the tube 61 is inserted into the primary bore 62 and is deflected by the cam surface 65 to the secondary bore 66 and then through the secondary bore 66 so that the tube extends beyond the opening 73. As the tube 61 and valve members 60 and 58 approach their final position as shown in FIG. 5, the flexible neck portion 95 strikes the cam surface 65 and is deflected towards and into the bore 66 and forms a seal between the tube 61 and the housing 56 at the bore 66 Since the bore 66 extends at a downward angle from the valve assembly 50 so that where the valve assembly 50 is inserted into the bottle 40, the opposite end of the tube contact the lower bottom most wall 45 of the bottle 40 as shown in FIG. 2. This ensures substantially all of the reagent within the bottle will be aspirated. The angle of the opening 66 also causes the inner end of the valve member 58 to become distorted due to the elastomeric nature of the valve member 58 as shown in FIG. 6. The inner second chamber 82 is operatively connected to the interior space 42 of the bottle through the tube 61.

Figure 21:
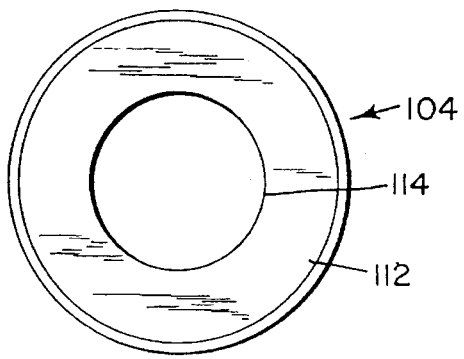
FIG. 21 is an outer end view of the cap potion of the cap assembly.
Figure 22:
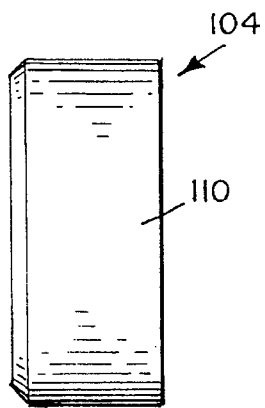
FIG. 22 is a side elevational view of the cap.
Figure 23:
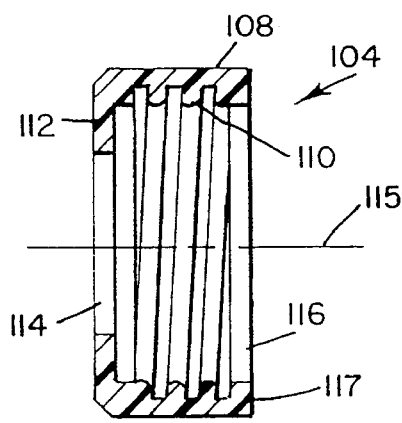
FIG. 23 is a vertical cross-sectional view of the cap.

Referring to FIG. 5, the cap assembly 52 comprises a cap, generally indicated by the reference numeral 104, and a thrust washer, generally indicated by the reference numeral 106. The details of the thrust washer 106 are shown in FIGS. 17–20. Details of the cap 104 are shown in FIGS. 21–23. Referring specifically to FIGS. 21–23, the cap 104 has a circular side wall 108 and an outer end wall 112 which is transverse to the side wall 108. The inner surface of the side wall 108 has internal threads 110. The end wall 112 has a circular outer opening 114 which is horizontally aligned with a circular inner opening 116 which is defined by the inner peripheral edge 117 of the side wall 108. The cap 104 has a central longitudinal axis 115 which extends through the centers of the openings 114 and 116.

Referring specifically to FIGS. 17–20, the thrust washer 106 has a circular side wall 118 and an inner end wall 119. The side wall 118 has an external ridge 122 and a plurality of slots 120 which cream a plurality of outwardly extending segments 121. The outer periphery of the side wall 118 defines an outer circular opening 124. The inner end wall 119 is transverse to the side wall 118 and has an inner circular opening 126. A circular inwardly facing flange 128 is located at the outer peripheral edge of the wall 119.

The cap assembly 52 is assembled by inserting the thrust washer 106 into the cap 104 so that the side wall 118 extends through the opening 114 of the cap. The outer diameter of the ridge 122 is slightly greater than the diameter of the circular opening 114. The thrust washer 106 and the cap are both constructed of a relatively rigid thermoplastic material by injection molding. However, the segments 121 of the thrust washer 106 are sufficiently resilient so as to be deflected toward the center of the opening 126 when they are forced against the peripheral edge of the opening 114. The ridge 122 has as outwardly facing beveled surface which forces each segment 121 of the wall 118 inwardly towards the central axis of the thrust washer when the wall 118 of the thrust washer is forced against the edge of the opening 114. This causes the wall 118 to be forced through the opening 114 of the wall 112 so that the external ridge 122 is located on the outside of the wall 112 and yieldably locks the thrust washer in position within the cap 104 as shown in FIG. 5. The thrust washer 106 is releasably locked against movement along the axis 115 relative to the cap 104 but is free to rotate about the axis 115 relative to the cap 104. Referring particularly to FIGS. 7–11, the fluid coupling means or coupler 54 comprises a horizontal main body portion 132 which has a central longitudinal axis 127. A connector fitting which is generally indicated by the reference numeral 130 is located at the outer end of the housing and a terminal nipple 134 is located at the inner end of the housing. The connector fitting 130 is adapted to be operatively connected to the complementary manifold fitting 55, see FIGS. 32–34, of aspirating means which forms part of an analytical instrument (not shown). The connector fitting 130 has an outer end surface 129 which has a circular groove 13 1. An elastomeric sealing ting 133 is located within the groove 131 and extends beyond the outer end surface 129. The connector fitting 130 has a relatively wide tab 137 and a relatively narrow tab 139. In the preferred embodiment, the tabs 137 and 139 are diametrically opposed and extend transversely of the longitudinal axis 127. Alternate positioning and configuration of the tabs of the connector firing may be accomplished to engage a respective manifold fitting. Tab 137 has an inwardly facing engaging surface 141. One end of the surface 141 has a bevel 143. A flange stop 145 is located at the opposite end of the surface 141 and extends inwardly and transversely of the surface 141. The tab 139 has an inwardly facing engaging surface 147. One end of the surface 147 has a bevel 149. An annular flange 136 extends transversely from the central longitudinal horizontal axis 127 and is located adjacent and spaced from the connector fitting 130. A pair of fingers 144 extends from the flange 136 toward the inner end of the main body portion 132. A longitudinal horizontal bore 138 extends from an outer opening 140 at the firing 130 through the main body portion 132 and the nipple 134 to an inner opening 142. The bore 138 functions as a liquid passageway. An annular groove 146 is located in the outer surface of the main body portion. A longitudinal groove 148 is located in the outer surface of the main body portion 132 and intersects the annular groove 146. The longitudinal groove 148 functions as a gas passageway. The coupling means 54 is operatively connected to the complementary manifold fitting 55 fixture of an analytical instrument which is capable of creating a suction at the opening 140.

Figure 32:
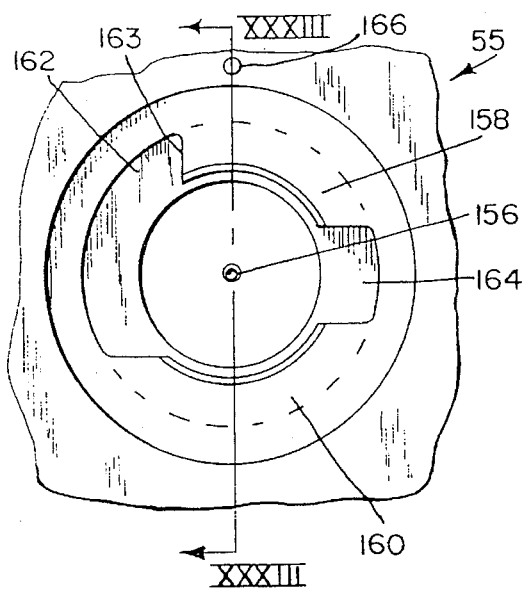
FIG. 32 is a front elevational view of a manifold fitting of an analytical instrument.
Figure 33:
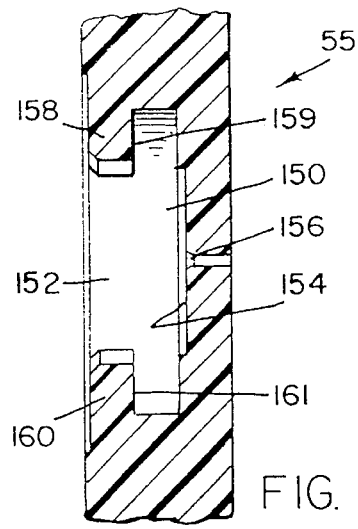
FIG. 33 is a vertical cross-sectional view of the manifold fitting taken along the line XXXIII—XXXIII of FIG. 32 and looking in the direction of the arrows.
Figure 34:
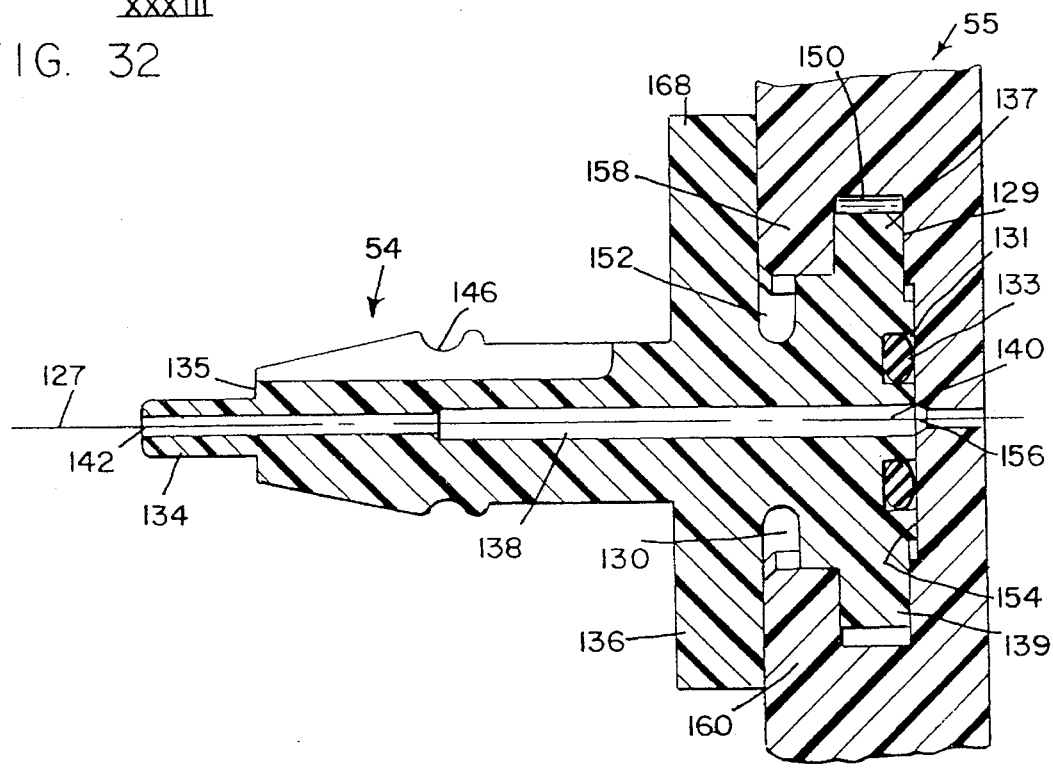
FIG. 34 is a vertical cross-sectional view of the coupling means operatively connected to the manifold fitting.

Referring to FIGS. 32–34, the manifold fitting 55 includes a manifold cavity 150 and a front opening 152 to the cavity. A fluid port 156 is located in an access surface 154 which forms the base of the cavity and which faces the front opening 152. The fluid port 156 is connected to a source of sub-atmospheric pressure, which is part of the analytical instrument (not shown). A first projection 158 and a second projection 160 extend toward each other at the opening 152.

The projections 158 and 160 are space from each other and define therebetween a first relatively wide slot 162 and a second relatively narrow slot 164. The projection 158 has an inner surface 159 which is space from and faces the access surface 154. The projection 160 has an inner surface 161 which is spaced from and faces the access surface 154.

The operation and advantages of a fluid delivery system of the present invention will now be readily understood in view of the above description. After the valve assembly 50 has been assembled as shown in FIG.6, it is inserted into the opening 48 of the bottle 40 as shown in FIG. 5.

The valve assembly 50 is applied to the bottle 40 by inserting the assembly into the bore 48 of the neck portion 44 of the bottle in a fixed predetermined position. The valve assembly is inserted so that the air vent 68 of the housing 56 faces upwardly and the tube 61 extends downwardly when the bottle 40 is in a generally horizontal position as shown in FIG. 2. The housing is fixed to the bottle in any one of several ways. In one embodiment of the invention, the housing is fixed to the neck of the bottle by fusing the flange 70 to the recessed annular edge 53 of the bottle, preferably by ultrasonic welding. When this procedure is used, the annular bead 72 functions as an energy director for the ultrasonic energy and is fused to the edge 53.

In another embodiment of the invention, the valve assembly 50 is fixed to the neck of the bottle by "press fitting" the housing 56 within the bore or opening 48. This is accomplished in one of two ways. A press fit is accomplished by making the outer diameter of the insertable portion of the housing slightly smaller than the diameter of the bore 48 so that the elongated beads 63 extend beyond the diameter of the bore 48. The housing 56 is then forced into the bore 48. The beads 63 distort due to the plastic composition of the housing and enable the housing to remain in the fixed predetermined position.

The valve assembly can also be press fitted into the bore 48 by making the outer diameter of the insertable portion of the housing slightly larger than the diameter of the bore 48. In this preferred embodiment, the inclusion of the beads 63 is optional. The tapered configuration of the main body portion 69 facilitates the press fitting of the housing 56.

The valve assembly can also be locked in the bottle by tab means 74 as described above.

The cap assembly 52 is then screwed onto the neck.44 of the bottle. As the cap assembly is rotated, the flanges 98, 89 and 70 are squeezed together. This provides a liquid and air-tight seal between the valve assembly and the bottle at the neck 44. When the cap assembly is tightened sufficient to cause friction between the thrust washer 106 and the elastomeric flange 98, the thrust washer 106 stops rotating with the cap as the cap continues to be turned in the advancing direction onto the neck 44. As a result, during the cap's torquing, the thrust washer applies only a horizontal force to the elastomeric flanges 98 and 89. This prevents twisting or distortion of the flanges 98 and 70 in any way except by direct horizontal compression as the cap is tightened. This also enables the cap to advance by compressing the flanges 89 and 98 until the inwardly facing flange 128 of the thrust washer engages the outer edge of the neck 44. This provides a positive and reproducible stop during the cap's torquing onto a bottle. This predetermined compression of the flanges 98 and 70 creates an ideal sealing condition. After the cap assembly 52 has been applied to the valve assembly and bottle, the bottle is thereby sealed against the flow of liquid or gas into or out of the bottle. This represents the first state of the valve assembly. The tube 61 creates a passageway for fluid in the bottle to the inner second chamber 82, but the wall 84 prevents the fluid from passing into the chamber 80. Air within the bottle is free to enter the first chamber 62 of the housing through the; air vent 68 and into the air ducts 86, but the second valve member 60 forms a seal at the openings 86 to prevent air from going beyond of the outer second chamber 80. A closure tab (not shown) is inserted into cap opening 114 to keep the valve assembly free of dust.

The connector fitting 130 of the coupling means 54 is operatively connected to the complementary manifold fitting 55. The connector fitting 130 is inserted into the cavity 150 of the manifold fitting 55 by aligning the tab 137 with the slot 162 and the tab 139 with the slot 164 and pushing the end surface 129 toward the access surface 154. The coupling means 54 is then rotated clockwise to a predetermined position as viewed in FIG. 34. The bevels 143 and 149 engage the inner surfaces 159 and 161, respectively and function as cam surfaces to guide the tabs 137 and 139 between each of the first and second projections 158 and 160, respectively, and the access surface 154. The bevels 143 and 149 are biased against the surfaces 159 and 161, respectively, by the elastomeric sealing ring 133. When the tabs 137 and 139 are positioned behind the projections 158 and 160, respectively, the sealing ring is compressed against the access surface 154 and forms a seal around the port 156. The coupling means 54 is rotated about the axis 127 for approximately 90°, at which point the flange 145 engages the adjacent edge 163 of the projection 158 to prevent further rotation. At this point, the longitudinal groove 148 faces upwardly as shown in FIG. 34. Connector fitting 130 of the coupling means 54 is operatively connected to the manifold fitting 55 as shown in FIG. 34. The opening 140 of the bore 138 is axially aligned with the port 156 so that the port 156 is operatively connected to the bore or liquid passageway 138.

The coupling means 54 is operatively connected to the valve assembly by moving the bottle toward the manifold so that the coupling means extends horizontally into the third chamber 92. When this occurs, the nipple 134 enters into the small diameter bore 93, thereby expanding the bore 93 and simultaneously expanding the slit 90 sufficiently to allow the nipple to penetrate the wall 84 and extend into the inner second chamber 82 as shown in FIG. 5. The shoulder 135 of the main body potion engages the wall 84 and forces the wall 84 away from the inner end of the second valve member 60, thereby creating a passageway between the chamber 62 and the chamber 80. When the coupling means 54 is fully inserted into the valve assembly 50 as shown in FIG. 5, the annular ridge 102 of-the second valve member engages the annular groove 146 of the coupling means 54 so that the coupling means is properly located within the valve assembly at a predetermined location relative to the valve assembly. At the same time, the fingers 144 engage the outer wall 112 of the cap 104 to prevent the coupling means from going beyond this predetermined position. The fingers 144 also function as finger grips for enabling an operator to easily connect and disconnect the coupling means 54 to the manifold fitting 55. When the coupling means 54 is properly located, the inner end of the groove 148 extends into the outer second chamber 80. The outer end of the groove 148 extends beyond the cap assembly 52 to create an air or gas passageway between the chamber 80 to a point outside of the bottle cap. When the bottle is connected to the coupling means 54, it is supported on a slightly inclined supporting tray 170, which forms part of the analyzing instrument (not shown). The bottle is supported in a substantially horizontal position and with a slight upward tilt toward the opening of the bottle due to the inclined angle of the supporting tray. The bottle is filled with fluid to the extent that the fluid is just below the air vent 68 and the groove 148 so that these elements lie in the air space above the top of the bottle above the fluid. This air space is minimal and filling of the bottle is maximized by the fact that the air vent 68 is located at the top of the housing 56, the groove 148 is located at the top of the coupling means 54, the neck 44 of the bottle 40 is located above the center line of the bottle and the bottle is tilted slightly upward toward the neck potion 4.4. When suction is applied at the opening 140 of the fitting 130, fluid or reagent is drawn from the bottle through the tube 61 to the chamber 82 and thence to the Opening 140 through the bore 138 of the coupling means 54 for further routing from the manifold for use by the analytical instrument. As reagent is drawn from the bottle, a volume of air or gas is drawn into the bottle through the passageway which is created by the groove 148, the chamber 80, openings 86, chamber 62 and opening 68.

Clearly, minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. A coupler for an aspirating fluid delivery system for conveying liquid from a source of liquid to be aspirated to a manifold fitting on an analytical instrument, said coupler comprising:

(a) a main body portion which has a central longitudinal axis, an elongated outer surface which is substantially parallel to said longitudinal axis, and an elongated liquid passageway which is substantially parallel to said longitudinal axis;

(b) a first end portion at one end of said main body portion which has a first end opening to said liquid passageway for operatively connecting said liquid passageway to said source of liquid; and (c) a second end portion at the opposite end of said main body portion from said one end, said second end portion having a connector fitting which is complementary with said manifold fitting, said connector fitting have a second end opening to said liquid passageway for connecting said liquid passageway to said manifold fitting, said connector fitting having a first tab which extends transversely away from said longitudinal axis and a second tab which extends transversely away from said longitudinal axis, one of said tabs having a stop flange at a first widthwise side of said one tab which extends toward said first end portion, said one tab having a bevelled cam surface at a second widthwise side of said one tab, said bevelled cam surface facing away from said stop flange and said first end portion.

2. A couple assembly for a fluid delivery system for aspirating liquid from a source of liquid to be aspirated to an analyzing instrument, said coupler assembly comprising:

(a) a manifold fitting for being operatively connected to an analyzing instrument, said manifold fitting having a cavity, an opening to the cavity, an access surface within said cavity and a fluid port in said access surface for operatively connecting the cavity to a source of sub-atmospheric pressure, (b) a coupler comprising:

(1) a main body portion which has a liquid passageway;

(2) a first end portion at one end of said main body portion for selectively operatively connecting said liquid passageway to said source of liquid to be aspirated:

(3) a second end portion at the opposite end of said main body portion from said one end portion, said second end portion having a connector fitting which is complementary with said manifold fitting, said connector fitting, having an end surface and an opening in said end surface to said liquid passageway; said connector fitting including means for releasably connecting said connector firing to said manifold fitting so that :said end surface faces said access surface and is urged toward said access surface and the opening in said end surface is aligned with said fluid port for operatively connecting said fluid port to said liquid passageway and to said source of liquid to be aspirated; and (4) sealing means for forming a seal between said end surface and said access surface around said fluid port and the opening in said end surface.

3. A coupler assembly for a fluid delivery system for aspirating liquid from a source of liquid to be aspirated to an analyzing instrument, said coupler assembly comprising:

(a) a manifold fitting for being operatively connected to an analyzing instrument, said manifold fitting having a cavity, an opening to the cavity, an access surface within said cavity and a fluid port in said access surface for operatively connecting the cavity to a source of sub-atmospheric pressure; and (b) a coupler comprising:

(1) a main body portion which has a central longitudinal axis, an elongated outer surface which is substantially parallel to said longitudinal axis, and an elongated liquid passageway which is substantially parallel to said longitudinal axis;

(2) a first end portion at one end of said main body portion which has a first end opening to said liquid passageway for operatively connecting said liquid passageway to said source of liquid; and (3) a second end portion at the opposite end of said main body portion from said one end portion, said second end portion having a connector fitting which is complementary with said manifold fitting, said connector fitting has an end surface which faces away from said first end portion, and which abuts said access surface when said connector fitting is connected to said manifold fitting, said end surface having a second end opening which is aligned with said fluid port for operatively connecting said fluid port to said liquid passageway and to said source of liquid to be aspirated, the end surface of said connector fitting having an annular groove which circumscribes said second end opening, said connector fitting having an elastomeric sealing ring which is located in said annular groove and which extends beyond said end surface for engaging said access surface for forming a seal between said end surface and said access surface around said fluid port and said second end opening.

4. A coupler assembly is recited in claim 3, wherein said coupler further comprises a flange which extends from the outer surface of said main body portion and which is spaced from said connector fitting.

5. A coupler assembly as recited in claim 4, wherein said coupler further comprises a stop finger which extends from said flange toward said first end portion.

6. A coupler assembly as recited in claim 4, wherein said flange is circular and has an annular outer edge surface which is parallel to said longitudinal axis, said outer edge surface having a protrusion for indicating the angular position of said coupler about said longitudinal axis.

* * * * *